United States Patent [19]

Takeda et al.

[11] Patent Number: 4,700,008

[45] Date of Patent: Oct. 13, 1987

[54] 4,8-DIMETHYLBICYCLO(3.3.1)NONANE DERIVATIVES

[75] Inventors: Makoto Takeda; Hiroshi Iwane; Akira Yoshida; Teruo Mori, all of Amimachi, Japan

[73] Assignee: Mitsubishi Yuka Fine Chemicals Co., Ltd., Tokyo, Japan

[21] Appl. No.: 554,926

[22] Filed: Nov. 25, 1983

[30] Foreign Application Priority Data

Dec. 20, 1982 [JP] Japan .................. 57-223258

[51] Int. Cl.$^4$ ............. C07C 49/105; C07C 43/18
[52] U.S. Cl. ............................. 568/374; 568/665
[58] Field of Search ............ 560/256; 568/374, 820, 568/665

[56] References Cited

FOREIGN PATENT DOCUMENTS 59826 10/1982 Japan .

OTHER PUBLICATIONS

Josephy, E. et al, Elsevier's Encyclopedia of Organic Chemistry, vol. 12A, Series III, Elsevier Publishing Co., Inc., 1948, 1057–1058.
Arctander, Perfume and Flavor Chemicals (Aroma Chemicals) I, Published by the Author, 1969, Montclair, N.J., monograph 352.
Schaefer et al, Chemical Abstracts, 69:43505K, 1968.
Wnuk et al, J. Org. Chem., vol. 40, No. 4, 1975, pp. 444 to 449.
Pelter et al, J. Chem. Society, Perkin Trans. I, 75, (2), pp. 129–138.

Primary Examiner—Werren B. Lone
Attorney, Agent, or Firm—Frishauf, Holtz, Goodman & Woodward

[57] ABSTRACT

There is disclosed a novel 4,8-dimethylbicyclo[3.3.1]nonane derivative represented by the formula [I]:

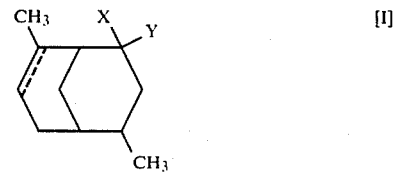

wherein X and Y have the same meanings as defined in the specification.

The compound of the present invention has an unique and strong perfume and hence is expected to be useful as perfumery.

9 Claims, 5 Drawing Figures

Magnified spectrum

4,8-DIMETHYLBICYCLO(3.3.1)NONANE DERIVATIVES

BACKGROUND OF THE INVENTION

This invention relates to a novel 4,8-dimethylbicyclo[3.3.1]nonane derivative, and more particularly, to a 4,8-dimethylbicyclo[3.3.1]nonane derivative having a unique and strong perfume and hence expected to be useful as perfumery.

The compound of the present invention is a novel bicyclic compound undisclosed in literatures and also a fragrant substance.

SUMMARY OF THE INVENTION

According to this invention, there is provided a novel 4,8-dimethylbicyclo[3.3.1]nonane derivative represented by the formula [I]:

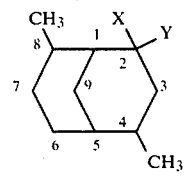

wherein one of X and Y represents a hydroxyl group, a straight or branched alkoxy group having 1 to 5 carbon atoms or an acyloxy group having 2 or 3 carbon atoms and the other represents a hydrogen atom, or they jointly represent an oxo group (=O); and a dotted line represents optional presence of a double bond.

DESCRIPTION OF THE PREFERRED EMBODIMENTS

Figure 1:
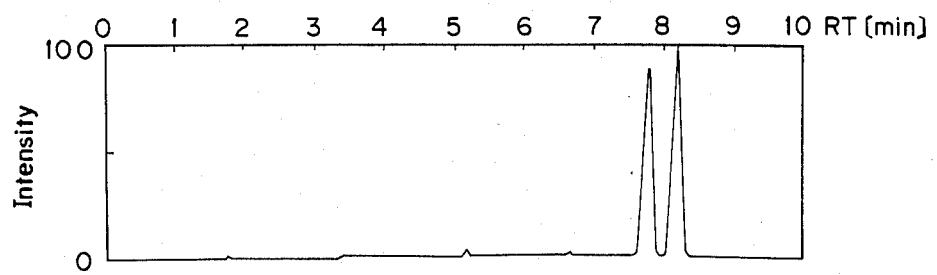
FIG. 1 shows a gas chromatogram of the product of Example 1.

The present compound can be prepared by subjecting 3-(4-methyl-3-cyclohexenyl)butyraldehyde (hereinafter referred to briefly as limonene aldehyde) [II] to intramolecular ring closure in the presence of an acid catalyst or further reducing the ring double bond thereof and furthermore by etherification, esterification or oxidation, as illustrated below. In particular, said intramolecular ring closure may proceed with an extremely high stereoselectivity.

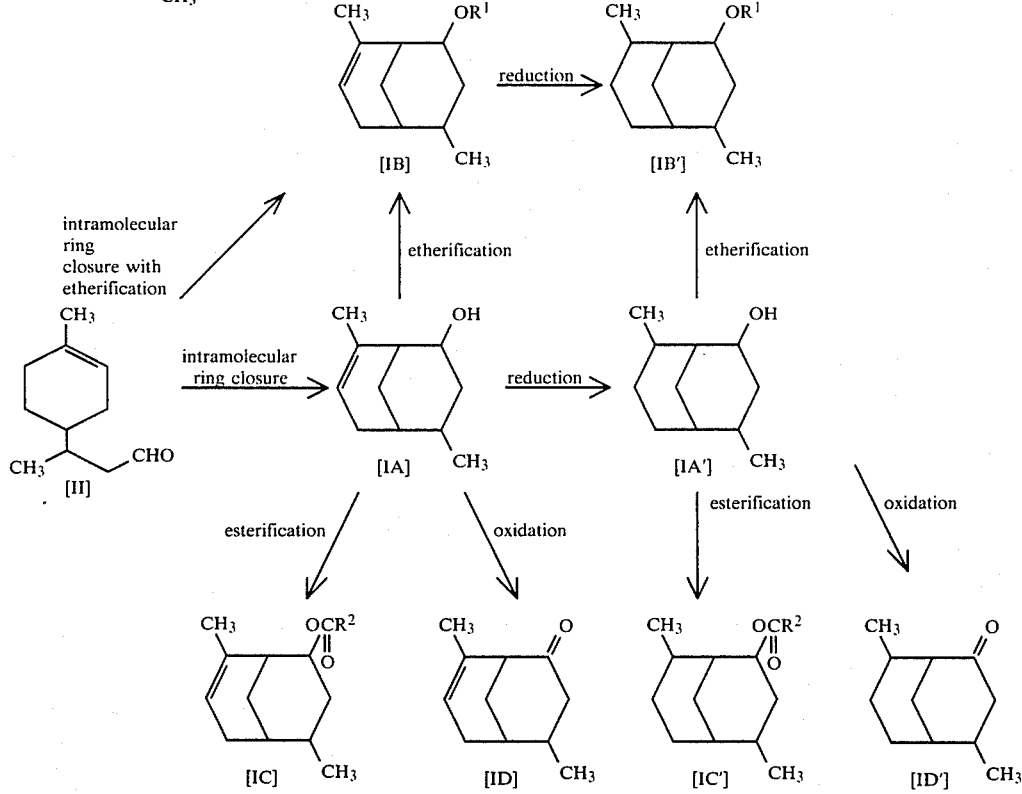

In the above formulae, $R^1$ represents a straight or branched alkyl group having 1 to 5 carbon atoms and $R^2$ represents a methyl group or an ethyl group. As the straight or branched alkyl group of 1 to 5 carbon atoms and represented by $R^1$, there may be mentioned a methyl group, an ethyl group, a n-propyl group, an isopropyl group, a n-butyl group, an isobutyl group, a n-amyl group, an isoamyl group, a sec-amyl group, a tert-amyl group and the like.

The (+) and/or (−) limonene aldehyde represented by the above-mentioned formula [II], which may be employed as a starting material in this invention, can be prepared through hydroformylation reaction of limonene as disclosed in Japanese Provisional Patent Publication No. 47638/1980. More specifically, said aldehyde can be prepared by the reaction of (+) and/or (−)-limonene with carbon monoxide and hydrogen. 4,8-dimethylbicyclo[3.3.1]nona-7-en-2-ol or its reduced product, 4,8-dimethylbicyclo[3.3.1]nona-2-ol, represented by the above formula [IA] or [IA'] can be prepared according to the process as depicted below. Namely, said alcohols can be prepared by subjecting (+) and/or (−)-limonene aldehyde [II] to intramolecular ring closure in the presence of an acid catalyst or by further reduction of the ring double bond. In particular, intramolecular ring closure may proceed with an extremely high stereoselectivity. More illustratively, the six types of the present compound as shown below can be prepared, for instance, from (+)-limonene.

Similarly, two types of stereoisomers of (1S,2S,5S)-4,8-dimethylbicyclo[[3.3.1]nona-7-en-2-ol and four types of stereoisomers of (1S, 2S, 5S)-4,8-dimethylbicyclo[3.3.1]nona-2-ol, which are in an enantiomerism relationship with the above-mentioned compounds, may be prepared from (−)-limonene aldehyde.

As the acid catalyst which may be employed for intramolecular ring closure reaction of limonene aldehyde, there may be mentioned, for example, an inorganic acid such as sulfuric acid, phosphoric acid or boric acid, an organic acid such as p-toluenesulfonic acid or benzenesulfonic acid and a strongly acidic cation exchange resin. An amount of the acid catalyst employed may be varied over a wide range, but 0.5 to 30% by weight, preferably 3 to 15% by weight, thereof may be usually suitable based on the starting limonene aldehyde.

Said intramolecular ring closure reaction may pro-

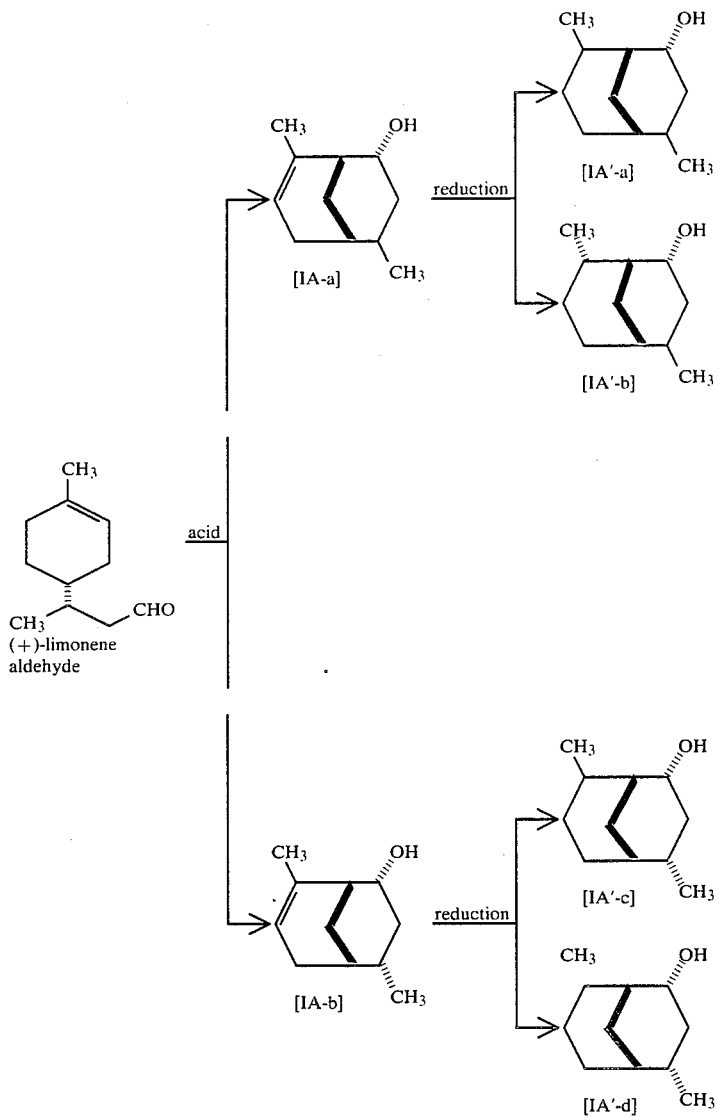

The compounds [IA-a] and [IA-b] are stereoisomers of (1R, 2R,5R)-4,8-dimethylbicyclo[3.3.1]nona-7-en-2-ol, while the compounds [IA'-a], [IA'-b], [IA'-c] and [IA'-d] are stereoisomers of (1R,2R,5R)-4,8-dimethylbicyclo [3.3.1]nona-2-ol, respectively.

ceed even in the absence of a solvent, but may proceed more smoothly in the presence of a solvent. As the solvent, there may be mentioned, for example, water, a lower carboxylic acid such as formic acid or acetic acid, a lower alcohol such as methanol or ethanol, an aliphatic or aromatic hydrocarbon such as hexane, benzene or toluene or a mixture thereof. A volume of the solvent employed is suitably 0.5 to 20 times, preferably 1 to 5 times, based on the limonene aldehyde. This reaction may smoothly proceed at a reaction temperature of 0° to 100° C., preferably 10° to 30° C.

The compound [IA'] can be prepared by a conventional catalytic hydrogenation reaction of the compound [IA]. As the catalyst which may be employed, there may be applied any catalysts commonly employed for catalystic hydrogenation such as palladium on carbon, Raney nickel or platinum oxide. An amount of the catalyst to be applied is 0.1 to 20% by weight, preferably 2 to 10% by weight, based on the 4,8-dimethylbicyclo[3.3.1]nona-7-en-2-ol. This reaction may proceed even in the absence of a solvent, but it is usually and preferably carried out in the presence of a solvent. A lower alcohol such as methanol or ethanol, acetic acid, dioxane or cyclohexane may be preferably employed. A volume of the solvent to be employed is suitably 0.5 to 20 times, preferably 1 to 5 times, based on the 4,8-dimethylbicyclo[3.3.1]nona-7-en-2-ol. This reaction may smoothly proceed at a reaction temperature of 0° to 150° C., preferably 50° to 100° C. and hydrogen pressure for reaction is 0.1 to 50 atm, preferably 1 to 30 atm.

As illustrative examples of the 4,8-dimethylbicyclo[3.3.1]nona-7-en-2-yl alkyl ether represented by the above formula [IB], there may be mentioned 4,8-dimethylbicyclo[3.3.1]nona-7-en-2-yl methyl ether, 4,8-dimethylbicyclo[3.3.1]nona-7-en-2-yl ethyl ether, 4,8-dimethylbicyclo[3.3.1]nona-7-en-2-yl isopropyl ether, 4,8-dimethylbicyclo[3.3.1]nona-7-en-2-yl isoamyl ether and the like. The compound [IB] may be prepared through intramolecular ring closure etherification reaction or etherification reaction of the limonene aldehyde [II] or 4,8-dimethylbicyclo[3.3.1]nona-7-en-2-ol [IA] with an alcohol compound [III] of the formula:

R$^1$OH  [III]

(wherein R$^1$ is the same as defined above) in the presence of an acid catalyst with removed of the water formed in situ. As the acid catalyst which may be employed for the above reaction, there may be mentioned, for example, an inorganic acid such as sulfuric acid, phosphoric acid or boric acid, an organic acid such as p-toluenesulfonic acid or benzenesulfonic acid and a strongly acidic cation exchange resin. An amount of the acid catalyst employed may be varied over a wide range, but 0.5 to 30% by weight, preferably 3 to 15% by weight, thereof may be usually suitable based on the starting limonene aldehyde [II] or the compound [IA]. An amount of the alcohol compound [III] employed is 2 to 20 times moles, preferably 5 to 15 times moles, based on the starting limonene aldehyde [II] or the compound [IA]. Reaction temperature is usually and preferably in the range of ordinary temperature to a reflux temperature of the alcohol compound [III].

As an alternative process, the compound [IB] may be also prepared by contacting the compound [IA] with an alkali metal or an alkali metal hydride in the presence of a suitable solvent to form the corresponding alkali metal salt and then reacting the salt as such, without isolation, with an alkyl halide. As the alkali metal or alkali metal hydride, there may be employed, for example, sodium, potassium, sodium hydride, lithium hydride and the like. An amount thereof to be used is 1 to 10 times moles, preferably 2 to 5 times moles, based on the compound [IA]. As the solvent, there may be mentioned, for example, benzene, toluene, tetrahydrofuran, dimethylformamide and the like. An amount thereof is 1 to 10 times, preferably 1 to 5 times in volume based on the compound [IA]. Reaction temperature is usually 0° to 100° C., preferably 20° to 80° C.

As illustrative examples of the 4,8-dimethylbicyclo[3.3.1]nona-2-yl alkyl ether having the above formula [IB'], there may be mentioned 4,8-dimethylbicyclo[3.3.1]nona-2-yl ethyl ether, 4,8-dimethylbicyclo[3.3.1]nona-2-yl isopropyl ether and the like. The compound [IB'] can be prepared by a conventional catalytic hydrogenation reaction of the compound [IB], in the same manner as mentioned in the preparation of the compound [IA'].

The compound [IB'] may also be prepared by etherification of the compound [IA']. This reaction can be effected in the same manner as done in the above-mentioned preparation of the compound [IB] using the acid catalyst, or alkali metal or alkali metal hydride.

As illustrative examples of the 4,8-dimethylbicyclo[3.3.1]nona-7-en-2-yl esters represented by the above formula [IC'], there may be mentioned 4,8-dimethylbicyclo[3.3.1]nona-7-en-2-yl acetate, 4,8-dimethylbicyclo[3.3.1]nona-7-en-2-yl propionate and the like.

Also, as illustrative examples of the 4,8-dimethylbicyclo[3.3.1]nona-2-yl esters represented by the above formula [IC'], there may be mentioned 4,8-dimethylbicyclo[3.3.1]nona-2-yl acetate and the like.

The compound [IC] or [IC'] may be prepared by esterifying the compound [IA] or [IA'] according to a conventional method, respectively. More specifically, the desired product can be easily produced by treating the compound [IA] or [IA'] with, for example, an acid halide such as acetyl chloride or propionyl chloride or an acid anhydride such as acetic anhydride or propionic anhydride. An amount of the acid halide or anhydride to be employed is 1 to 2 times moles, preferably 1 to 1.2 times moles, based on the compound [IA] or [IA']. This reaction can be advantageously carried out in the presence of an organic base such as pyridine, triethylamine and the like. An amount of these organic base to be used is 1 to 2 times moles, preferably 1 to 1.2 times moles, based on the acid halide or anhydride. The reaction may proceed even in the absence of a solvent, but it is usually preferred to use a suitable solvent such as benzene, toluene, tetrahydrofuran or dioxane. A volume of the solvent to be employed is 1 to 10 times, preferably 1 to 5 times based on the compound [IA] or [IA']. Reaction temperature is 0° to 100° C., preferably 20° to 80° C.

4,8-Dimethylbicyclo[3.3.1]nona-7-en-2-one represented by the formula [ID] and 4,8-dimethylbicyclo[3.3.1]nona-2-one represented by the formula [ID'] can be prepared by oxidation of the compound [IA] and [IA'] according to a conventional method, respectively. As the oxidizing agent which may be employed, there may be mentioned, for example, chromic acid, silver oxide, potassium permanganate or potassium dichromate. An amount of the oxidizing agent to be employed is 1 to 10 times moles, preferably 1 to 3 times moles, based on the compound [IA] or [IA']. A solvent may be preferably employed and, as preferred solvents, there may be mentioned, for example, water, acetone, hexane, benzene and the like. An amount of the solvent to be used is 1 to 20 times in volume, preferably 5 to 15 times, based on the compound [IA] or [IA']. Reaction temperature is −10° to 30° C., preferably −5° to 25° C.

This invention will be more fully explained by way of the following examples, but they are not contemplated to be limiting the scope of this invention.

EXAMPLE 1

A mixture of 80 g of (+)-limonene aldehyde $[[\alpha]_D^{25} = +98.3° (c=2.2, CHCl_3)]$, 100 ml of water, 30 ml of acetic acid and 7 ml of conc. sulfuric acid was reacted under stirring for 12 hours at a reation temperature of 25°-30° C. After completion of the reaction, an organic layer was separated, neutralized and the water with saturated aqueous sodium hydrogen carbonate, washed with water and then dried over magnesium sulfate. Subsequently distillation under reduced pressure gave 67.9 g of (1R,2R,5R)-4,8-dimethylbicyclo[3.3.1]nona-7-en-2-ol, which had a camphor-like smell.

b.p.: 86°-90° C./0.6 mmHg (Yield: 84.9%)

$[\alpha]_D^{25} = +157.4° (c=2.1, CHCl_3)$

In this compound, there are presumed four types of isomers with regard to steric configuration at the 2- and 4-positions thereof, but analysis of the following analytical results revealed that this compound is an approximately 1:1 equimolar mixture of the compound of the formula [IA-b] having the endo-methyl group at the 4-position thereof and the endo-hydroxyl group at the 2-position thereof and the compound of the formula [IA-a] having the exo-methyl group at the 4-position thereof and the same hydroxyl group.

(1) Gas chromathography (See FIG. 1)

Gas chromatography was effected by using 25 m of a fused silica capillary column coated with polyethylene glycol and having an inner diameter of 0.31 mm under conditions of a hydrogen flame detector of 2.0 cc/min. of a carrier gas flow rate, 150° C. of a column temperature. As a result, two peaks were detected with areas of 48.0% and 49.9% at 7.84 minutes and 8.26 minutes, respectively.

(2) Gas chromatographic mass spectrometry analysis

Measurement was done under the same condition as in the above gas chromatography and mass spectra of the said two peaks showed molecular ion $M^+$ of 166 ($C_{11}H_{18}O$). Also, both mass spectral patterns are closely similar, which demonstrates that these compounds are stereoisomers which are difficult to distinguish by their respective mass spectra.

Figure 2:
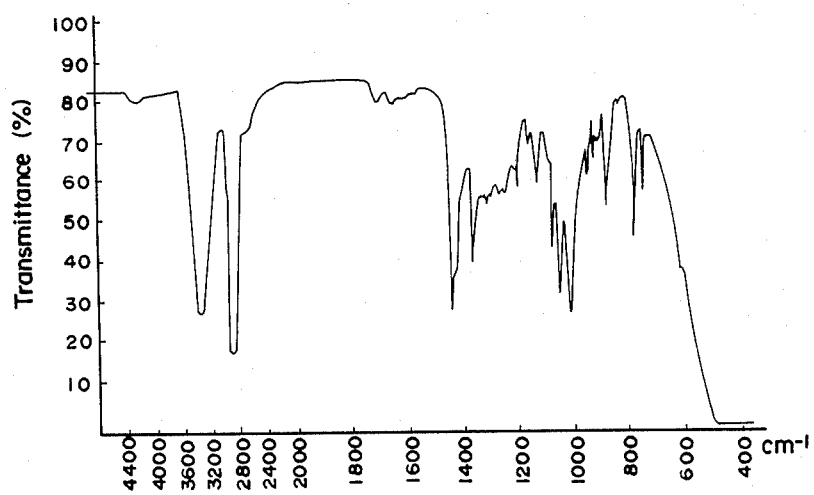
FIG. 2 shows an infrared absorption spectrum of the product of Example 1.

(3) Infrared absorption spectrum (See FIG. 2)

The following characteristic absorption bands were observed:

| | |
|---|---|
| 3400 cm$^{-1}$ | (O—H, streching vibration) |
| 3020 cm$^{-1}$ | (C—H, —CH=C—, streching vibration) |
| 1660 cm$^{-1}$ | (C=C, streching vibration) |
| 802 cm$^{-1}$ | (C—H, —CH=C—, out-of-plane vibration). |

Thus, presence of a hydroxyl group and a tri-substituted double bond was confirmed, but no carbonyl group observed.

(4) NMR spectrum $H^1$-NMR spectrum was measured in a deuterochloroform solution at a resonance frequency of 269.65 MHz, while $C^{13}$-NMR spectrum at a resonance frequency of 67.80 MHz. Measurement of pseudo-contact shift in the $C^{13}$-NMR using as a shift reagent tris(-dipivalomethane)europium proved a relationship of steric configuration between respective atoms forming a molecule. Also, structure of each carbon atom type (primary, secondary, tertiary and quaternary carbons) was determined by using off-resonance. Because of co-existence of two types of isomers, two chemical shifts in each group except for the methyl group located at the 8-position thereof were observed and a total of 21 peaks was observed.

Figure 3:
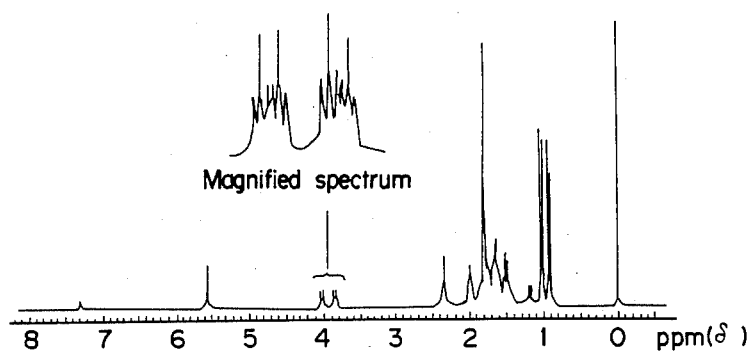
FIG. 3 shows a $H^1$-nuclear magnetic resonance spectrum of the product of Example 1.

The $H^1$-NMR (See FIG. 3) showed the following absorptions:

| | |
|---|---|
| δ ppm 5.54 | olefinic hydrogen |
| δ ppm 4.40 | hydrogen adjacent to hydroxyl group (2-position) |
| δ ppm 3.83 | hydrogen adjacent to hydroxyl group (2-position) |
| δ ppm 1.78 | 8-methyl |
| δ ppm 1.03 | 4-methyl |
| δ ppm 0.92 | 4-methyl |

Figure 4:
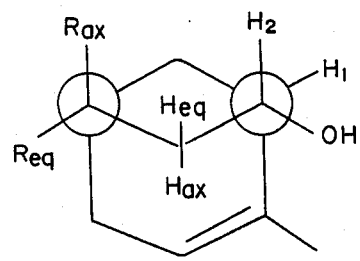
FIG. 4 shows a Newman's projection formula of the product of Example 1.

Steric configuration of the 2-hydroxyl group has been proved to be "endo" from the splitting pattern of the absorption lines in the 2-hydrogen ($H_2$) was spin-bonded to Hax at 10.5 Hz and to Hex and $H_1$ at 3.9 Hz and thus is "endo" as shown in FIG. 4 according to Karplus' rule.

EXAMPLE 2

Into a 50 cc glass autoclave were charged 5.5 g of the (1R,2R,5R)-4,8-dimethylbicyclo[3.3.1]nona-7-en-2-ol obtained in the above Example 1, 1.0 g of 5% Pd/C and 25 ml of ethanol and the reaction was effected by heating under stirring at reaction hydrogen pressure of 3 to 5 atm and a temperature of 70° C. over 3 hours. After cooling, the content was removed from the autoclave, the catalyst was filtered off and the solvent was distilled off from the filtrate under reduced pressure to give 5.3 g of semi-crystalline (1R,2R,5R)-4,8-dimethylbicyclo[3.3.1]nona-2-ol, which had a menthol-like smell.

This compound was proved from the following analytical results to be a mixture of the 4-endo, 8-endo compound of the formula [IA'-a], the 4-endo, 8-exo compound of the formula [IA'-b], the 4-exo, 8-endo compound of the formula [IA'-c] and the 4-oxo, 8-exo compound of the formula [IA'-d].

The (1R,2R,5R)-4,8-dimethylbicyclo[3.3.1]nona-7-en-2-ol obtained in the above Example 1 is a 1:1 equimolar mixture of the two isomers and hence the compound obtained from hydrogenation of the former disappeared a double bond and the 8-carbon newly became an asymmetric carbon atom, whereby 4 types of isomers were formed.

Figure 5:
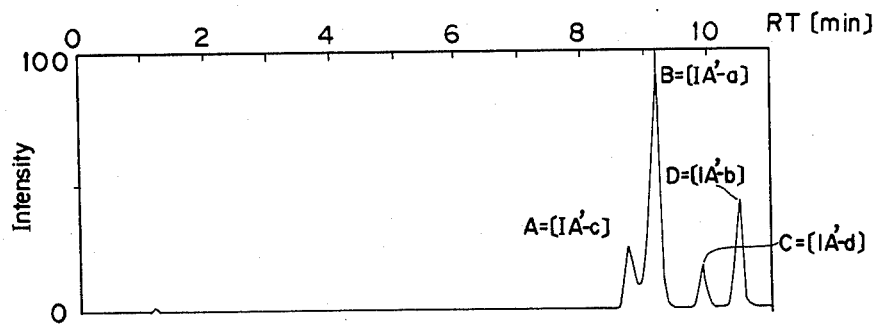
FIG. 5 shows a gas chromatogram of the product of Example 2.

(1) Gas chromatography (See FIG. 5)

Gas chromatogram was measured under the same conditions as in the above Example 1 to detect 4 peaks at 7.27 minutes, 7.53 minutes, 8.07 minutes and 8.46 minutes, respectively. Respective area were designated A, B, C and D, respectively, in the order of the corresponding component effusion.

This mixture is in a liquid state at ordinary temperature, but, when dissolved in n-hexane and ice-cooled, it partly crystallizes. As B and C are concentrated in the said crystalline substance, it may be said that the B and C are liable to crystallize easily.

(2) Gas chromatographic mass spectrometry analysis

Each mass spectrum was obtained through maesurement under the same conditions as in the gas chromatography to show a molecular ion M+ 168 ($C_{11}H_{20}O$) and a closely similar mass spectral pattern in every case. The presence of dehydrated peak M+ −18 (M/Z 150) existing when ionized proved the presence of a hydroxyl group.

(3) NMR spectrum $C^{13}$-NMR spectrum was taken in a deuterichloroform solution in the same manner as in the above Example 1. By corresponding an approximate concentration of each component from gas chromatogram to each peak strength in the $C^{13}$-NMR spectrum, carbon atoms in respective A, B, C and D components were assigned to chemical shift of some peaks. Moreover, assignment to each component became clear from chemical shift of the carbon which the 2-hydroxyl group is particularly attached to, whereby structures of 4 components were confirmed. Namely, where the 4-methyl group is exo and the 8-methyl group is endo, it is believed that γ-effect can be induced by $C^{13}$-chemical shift at the 2-position and thus a high magnetic field of 3 to 6 ppm can be induced. Then, the component D with the highest magnetic field is the 4-exo, 8-endo component of the formula [IA′-b], while the component A with the lowest magnetic field is the 4-endo, 8-exo compound of the formula [IA′-c]. As the compound before hydrogenation was a 1:1 mixture of the 4-exo and 4-endo types, steric configuration at the 4-position should be identical between the component A and the component C or between the component B and the component D. Accordingly, it has been determined that the component B is the 4-exo, 8-exo compound of the formula [IA′-a] and the component C is the 4-endo, 8-endo compound of the formula [IA′-d].

39 Numbers of chemical shift peaks were detected, while two of them were overlapped. With regard to methyl groups located at the 4- and 8-positions, a total of 8 peaks was to be detected, but 3 of them were equivalent. Thus, 5 methyl groups were observed. A sort of carbons was classified according to an INEPT method.

EXAMPLE 3

Following the same reaction procedures as in Example 1 except that 15 g of (−)-limonene aldehyde [$[\alpha]_D^{25} = -48.7°$ (c=2.1, $CHCl_3$)] were employed, there were obtained 12.5 g of (1S,2S,5S)-4,8-dimethylbicyclo[3.3.1]nona-7-en-2-ol, which had a camphor-like smell.

b.p.: 83°–84° C./0.4 mmHg (Yield: 83.3%),
$[\alpha]_D^{25} = -84.4°$ (c=2.0, $CHCl_3$).

This compound is in an enantiomerism relationship with the compound as obtained in Example 1 and analytical results of gas chromatography, gas chromatographic mass spectrometry analysis, infrared absorption spectrum and NMR spectrum of this compound were identical with those of the compound obtained in Example 1.

EXAMPLE 4

Following the same reaction procedures as in Example 2 except that 6.0 g of (1S,2S,5S)-4,8-dimethylbicyclo[3.3.1]nona-7-en-2-ol obtained in Example 3 were employed, there were obtained 5.7 g of (1S,2S,5S)-4,8-dimethylbicyclo[3.3.1]nona-2-ol as a semi-crystalline substance, which had a menthol-like smell.

This compound is in an enantiomerism relationship with the compound as obtained in Example 2 and analytical results of gas chromatography, gas chromatographic mass spectrometry analysis, infrared absorption spectrum and NMR spectrum of this compound were identical with those of the compound obtained in Example 2.

EXAMPLE 5

Synthesis of 4,8-dimethylbicyclo[3.3.1]nona-7-en-2-yl isopropyl ether [IB]

To a solution of 10 g (60.2 mmol) of (+)-limonene aldehyde in 40 ml of isopropyl alcohol was added 1 g of Amberlyst 15 (produced by Rohm & Haas Co.) as a strongly acidic cation exchange resin and the resulting mixture was heated under reflux for 15 hours. After cooling, the Amberlyst 15 was filtered off and then the isopropyl alcohol was distilled off. The residue was subjected to column chromatography and eluate with toluene gave 10.4 g of the title compound, which had a sweet, camphor-like smell.

Yield: 83%, $n_D^{23} = 1.4747$
NMR ($CDCl_3$) δ ppm; 0.95 (3H, d), 1.17 (6H, d), 1.1–2.8 (12H, m), 3.5 (1H, m), 3.72 (1H, qq), 5.5 (1H, m).
IR (liquid film) $cm^{-1}$; 2950, 2910, 2870, 1660, 1447, 1374, 1361, 1330, 1170, 1141, 1121, 1095, 1080, 1060, 983, 800.

EXAMPLES 6

Synthesis of 4,8-dimethylbicyclo[3.3.1]nona-7-en-2-yl ethyl ether [IB]

Following the same procedures as in Example 5 except that there were employed 16.6 g (100 mmol) of (+)-limonene aldehyde, there were obtained 16.5 g of the title compound, which had a fresh, refrigerant and pinene-like smell.

Yield: 85%, $n_D^{23} = 1.4813$
NMR ($CDCl_3$) δ ppm; 0.95 (3H, d), 1.18 (3H, t), 1.1–2.8 (12H, m), 3.3 (1H, m), 3.5 (2H, q), 5.5 (1H, m).
IR (liquid film) $cm^{-1}$; 2930, 2900, 2860, 1660, 1442, 1365, 1341, 1105, 1074, 800.

EXAMPLE 7

Synthesis of 4,8-dimethylbicyclo[3.3.1]nona-7-en-2-yl isoamyl ether [IB]

Following the same procedures as in Example 5 except that there were employed 16.6 g (100 mmol) of (−)-limonene aldehyde, there were obtained 19.1 g of the title compound, which had a fresh and camphor-like smell.

Yield: 81%, $n_D^{23} = 1.4768$
NMR ($CDCl_3$) δ ppm; 0.95 (9H, d), 1.0–2.8 (15H, m), 3.3 (1H, m), 3.45 (2H, t), 5.5 (1H, m).
IR (liquid film) $cm^{-1}$; 2950, 2910, 2880, 1660, 1450, 1362, 1348, 1100, 800.

EXAMPLE 8

Synthesis of 4,8-dimethylbicyclo[3.3.1]nona-7-en-2-yl methyl ether [IB]

To a solution of 10 g (60.2 mmol) of 4,8-dimethylbicyclo[3.3.1]nona-7-en-2-ol [IA] in 60 ml of tetrahydrofuran were added 1.3 g (56.5 mmol) of sodium and the resulting mixture was heated with stirring at 40° C. After the sodium was dissolved, 12.8 g (90 mmol) of methyl iodide were added dropwise and the resulting mixture was heated with stirring at 40° C. for 10 hours. After cooling, the tetrahydrofuran was distilled off under reduced pressure, the residue was subjected to column chromatography and eluate with toluene gave 7.8 g of the title compound, which had a refrigerant and camphor-like smell.

Yield: 72%, $n_D^{23} = 1.4867$

NMR (CDCl$_3$) δ ppm; 0.95 (3H, d), 1.0–2.8 (12H, m), 3.37 (3H, s), 3.5 (1H, m), 5.5 (1H, m).

IR (liquid film) cm$^{-1}$; 2910, 2870, 2810, 1660, 1445, 1370, 1190, 1100, 798.

EXAMPLE 9

Synthesis of 4,8-dimethylbicyclo[3.3.1]nona-2-yl methyl ether [IB']

To a solution of 1 g (5.6 mmol) of 4,8-dimethylbicyclo[3.3.1]nona-7-en-2-yl methyl ether [IB] in 10 ml of ethanol was added 0.1 g of 5% of Pd/C and the resulting mixture was heated with stirring at a hydrogen pressure of 20 atm and a reaction temperature of 70° C. for 6 hours. After cooling, the Pd/C was filtered off and the ethanol was distilled off under reduced pressure. The residue was subjected to column chromatography and eluate with toluene gave 0.95 g of the title compound, which had a camphor-like smell.

Yield: 94%, $n_D^{23} = 1.4751$

NMR (CDCl$_3$) δ ppm; 0.95 (3H, d), 1.0–2.8 (15H, m), 3.33 (3H, s), 3.5 (1H, m).

IR (liquid film) cm$^{-1}$; 2950, 2910, 2860, 1480, 1450, 1372, 1190, 1105, 990.

EXAMPLE 10

Synthesis of 4,8-dimethylbicyclo[3.3.1]nona-7-en-2-yl acetate [IC]

To a solution of 10 g (60.2 mmol) of 4,8-dimethylbicyclo[3.3.1]nona-7-en-2-ol [IA] in 40 ml of tetrahydrofuran were added 6.8 g (66.6 mmol) of acetic anhydride and 5.2 g (65.7 mmol) of pyridine and the resulting mixture was heated under reflux for 5 hours. After cooling, the tetrahydrofuran was distilled off, the residue was subjected to column chromatography and eluate with toluene gave 10.9 g of the title compound, which had a woody-like smell.

Yield: 87%, $n_D^{23} = 1.4850$

NMR (CDCl$_3$) δ ppm; 0.95 (3H, d), 1.1–2.3 (10H, m), 2.03 (3H, s), 2.4 (2H, m), 5.0 (1H, m), 5.6 (1H, m).

IR (liquid film) cm$^{-1}$; 3000, 2950, 2920, 2830, 1730, 1450, 1375, 1363, 1245, 1053, 1025, 800.

EXAMPLE 11

Synthesis of 4,8-dimethylbicyclo[3.3.1]nona-2-yl acetate [IC']

Following the same procedures as in Example 10, 11.5 g of the title compound were obtained from 10.0 g (59.4 mmol) of 4,8-dimethylbicyclo[3.3.1]nona-2-ol [IA']. This compound had a woody-like smell.

Yield: 92%, $n_D^{23} = 1.4754$

NMR (CDCl$_3$) δ ppm; 0.95 (3H, d), 1.12 (3H, d), 1.1–2.8 (12H, m), 2.01 (3H, s), 5.1 (1H, m).

IR (liquid film) cm$^{-1}$; 2950, 2925, 2870, 1740, 1482, 1450, 1370, 1243, 1025.

EXAMPLE 12

Synthesis of 4,8-dimethylbicyclo[3.3.1]nona-7-en-2-yl propionate [IC]

Following the same procedures as in Example 10 except that propionyl chloride was employed in place of acetic anhydride, 6.0 g of the title compound were obtained from 5.0 g (30.1 mmol) of 4,8-dimethylbicyclo[3.3.1]nona-7-en-2-ol [IA]. This compound had a woody-like smell.

Yield: 90%, $n_D^{23} = 1.4821$

NMR (CDCl$_3$) δ ppm; 0.95 (3H, d), 1.16 (3H, t), 1.1–2.8 (12H, m), 2.02 (2H, q), 5.1 (1H, m), 5.6 (1H, m).

IR (liquid film) cm$^{-1}$; 2930, 2910, 2870, 2825, 1730, 1450, 1372, 1353, 1340, 1180, 1075, 1010, 800.

EXAMPLE 13

Synthesis of 4,8-dimethylbicyclo[3.3.1]nona-7-en-2-one [ID]

To a solution of 5 g (30.1 mmol) of 4,8-dimethylbicyclo[3.3.1]nona-2-ol [IA] in 30 ml of acetone was added dropwise a solution of 6 g (60.2 mmol) of chromic acid in 20 ml of 20% sulfuric acid and the resulting mixture was stirred at 0° C. for 3 hours. To the reaction mixture were added 100 ml of water and the resulting mixture was extracted with 30 ml of toluene. The toluene was distilled off under reduced pressure, the residue was subjected to column chromatography and eluate with toluene gave 4.2 g of the title compound, which had a fruity, jasmine-like smell.

Yield: 85%, $n_D^{23} = 1.5030$

NMR (CDCl$_3$) δ ppm; 1.06 (3H, d), 1.4–3.2 (12H, m), 5.6 (1H, m).

IR (liquid film) cm$^{-1}$; 2940, 2900, 1703, 1660, 1442, 1375, 1270, 1220, 808.

EXAMPLE 14

Synthesis of 4,8-dimethylbicyclo[3.3.1]nona-2-one [ID']

Following the same procedures as in Example 13, 10.0 g (60.2 mmol) of 4,8-dimethylbicyclo[3.3.1]nona-2-ol [IA'] gave 8.0 g of the title compound, which had a floral, menthol-like smell.

Yield: 81%, $n_D^{23} = 1.4852$

NMR (CDCl$_3$) δ ppm; 0.87 (3H, d), 1.07 (3H, d), 1.0–2.8 (12H, m).

IR (liquid film) cm$^{-1}$; 2940, 2910, 2860, 1770, 1450, 1410, 1374, 1237.

We claim:

1. A 4,8-dimethylbicyclo-[3.3.1]nona-7-en-2-yl alkyl ether selected from the group consisting of 4,8-dimethylbicyclo[3.3.1]nona-7-en-2-yl methyl ether, 4,8-dimethylbicyclo[3.3.1]nona-7-en-2-yl ethyl ether, 4,8-dimethylbicyclo[3.3.1]nona-7-en-2-yl isopropyl ether and 4,8-dimethylbicyclo[3.3.1]nona-7-en-2-yl isoamyl ether.

2. The ether of claim 1, which is 4,8-dimethylbicyclo[3.3.1]nona-7-en-2-yl methyl ether.

3. The ether of claim 1, which is 4,8-dimethylbicyclo[3.3.1]nona-7-en-2-yl ethyl ether.

4. The ether of claim 1, which is 4,8-dimethylbicyclo[3.3.1]nona-7-en-2-yl isopropyl ether.

5. The ether of claim 1, which is 4,8-dimethylbicyclo[3.3.1]nona-7-en-2-yl isoamyl ether.

6. 4,8-dimethylbicyclo[3.3.1]nona-7-en-2-one.

7. A 4,8-dimethylbicyclo[3.3.1]nona-2-yl alkyl ether selected from the group consisting of 4,8-dimethylbicyclo[3.3.1]nona-2-yl ethyl ether, and 4,8-dimethylbicyclo[3.3.1]nona-2-yl isopropyl ether.

8. The ether of claim 7, which is 4,8-dimethylbicyclo[3.3.1]nona-2-yl ethyl ether.

9. The ether of claim 7, which is 4,8-dimethylbicyclo[3.3.1]nona-2-yl isopropyl ether.

* * * * *